United States Patent [19]

Reul et al.

[11] 4,263,680

[45] Apr. 28, 1981

[54] PROSTHETIC CLOSURE DEVICES TO REPLACE THE VALVES IN HUMAN HEARTS

[75] Inventors: Helmut Reul, Düren; Ernst-Wilhelm Müller, Bornheim-Merten, both of Fed. Rep. of Germany

[73] Assignee: Beiersdorf, AG, Hamburg, Fed. Rep. of Germany

[21] Appl. No.: 21,962

[22] Filed: Mar. 19, 1979

[30] Foreign Application Priority Data

Apr. 12, 1978 [DE] Fed. Rep. of Germany ....... 2815756

[51] Int. Cl.³ .............................................. A61F 1/22
[52] U.S. Cl. ......................................... 3/1.5; 137/527
[58] Field of Search ................... 3/1.5; 137/527, 527.8

[56] References Cited

U.S. PATENT DOCUMENTS

| | | | |
|---|---|---|---|
| 399,390 | 3/1889 | Eareckson | 137/527 |
| 1,233,391 | 7/1917 | Mullane et al. | 137/527.8 X |
| 1,827,913 | 10/1931 | Rymal | 137/527.8 |
| 2,930,400 | 3/1960 | Wheatley | 137/527.8 |
| 3,370,305 | 2/1968 | Goott et al. | 3/1.5 |
| 3,538,514 | 11/1970 | Schimert et al. | 3/1.5 |
| 3,722,004 | 3/1973 | Cromie | 3/1.5 |
| 3,857,408 | 12/1974 | Rhodes et al. | 137/527 X |
| 4,057,857 | 11/1977 | Fettel | 3/1.5 |

FOREIGN PATENT DOCUMENTS

| | | | |
|---|---|---|---|
| 2212551 | 10/1972 | Fed. Rep. of Germany | 3/1.5 |
| 2313271 | 9/1973 | Fed. Rep. of Germany | 3/1.5 |

OTHER PUBLICATIONS

Seidel, et al. "Herzklappenprothesen", *Deutsche Medizinische Wochenzeitschrift*, 88Jg. No. 15, 12 Apr., 1963, pp. 748–754.

*Primary Examiner*—Clifford D. Crowder
*Attorney, Agent, or Firm*—Andrus, Sceales, Starke & Sawall

[57] ABSTRACT

A prosthetic closure device to replace a human heart valve, in particular the mitral or tricuspid valve, comprises an annular valve body, around the periphery of which a suture ring is provided for attaching the valve body to the heart tissue, and a valve member located in the valve body. The valve member is in the form of a spherical segment having a diameter of 1.058 $D_{ri}$ and comprising part of the surface of a hollow sphere having a diameter of $2D_{ri}$, where $D_{ri}$ is the smallest inner diameter of the valve body. The valve member is hinged to the valve body by means of a flap formed integrally with the valve member and which projects through a slot in the valve body, where it is secured by the suture ring, to form a hinge. The inner surface of the valve body narrows conically in the direction of inflow and subsequently widens to provide an annular seating for the valve member.

14 Claims, 3 Drawing Figures

U.S. Patent
Apr. 28, 1981
4,263,680
Fig.1
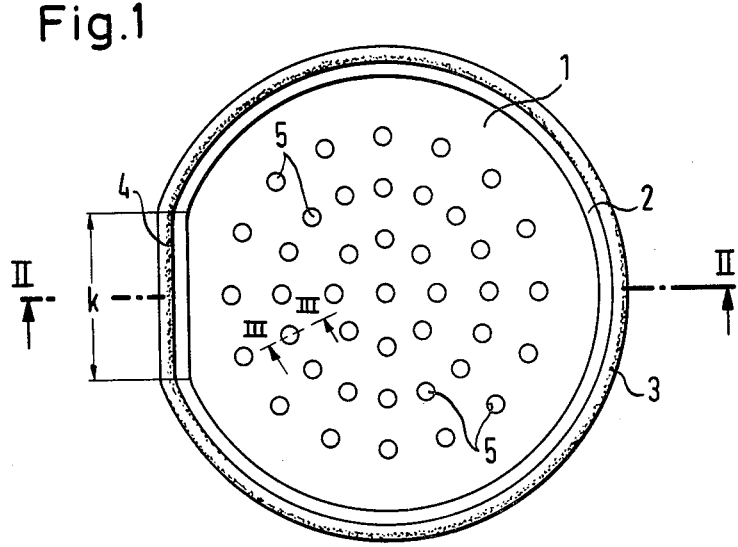
Fig.2
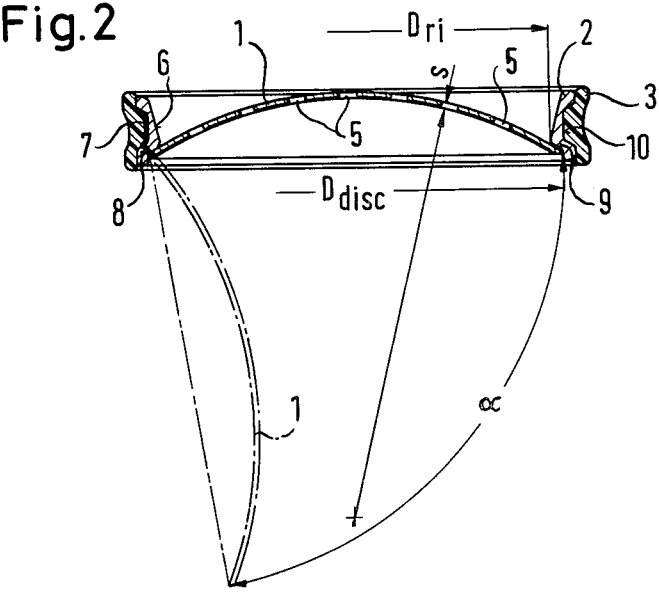
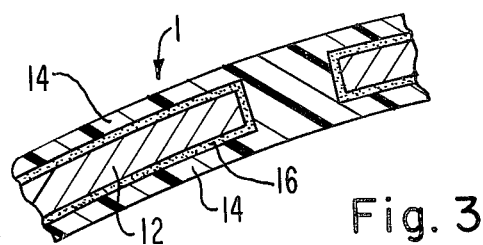
Fig. 3

PROSTHETIC CLOSURE DEVICES TO REPLACE THE VALVES IN HUMAN HEARTS

BACKGROUND OF THE INVENTION

This invention relates to prosthetic closure devices to replace the valves in human hearts, in particular the mitral and tricuspid valves, having a valve body in the form of a ring, a suture ring for attaching the valve body to the tissue and a valve member positioned in the valve body.

The history of artificial heart valves already covers a period of over twenty-five years and began with the first valve implanted by Hufnagel in 1952. Since then the problems of developing and perfecting artificial heart valves have not been completely solved, which results in the large number of around forty types of valves in use today.

At present spherical and disc valves are the leaders in the field, and also in the last few years replacement valves for special uses made from pig's heart valves have also gained in importance. However, the results obtained with all closure devices of this type are not satisfactory. For example, the average survival rate of patients with an artificial heart valve is still under five years.

The resultant complications can essentially be reduced to four reasons:
 flow mechanics reasons,
 mechanical reasons,
 biological reasons,
 material reasons,
or combinations of these four.

Mechanical reasons for a valve defect can be material fatigue, breakage or deformation of a valve either due to mechanical stress or chemical corrosion. Amongst defects of a biological nature, inflammation and rejection of the material which is foreign to the body are frequently encountered. Defects due to flow mechanics, such as destruction of red corpuscles in areas of high localised shear stress and the formation of thromboses in areas of low speed of flow, are further important reasons. Shear stress and distribution of speed with the above-mentioned characteristics are to be found in all valves, since they restrict the blood flow in various ways:

(a) by the valve member itself, which forces the blood to flow through an annular slot between the valve member and the valve body (with spherical or disc valves) or in two separate flow channels with a different form of flow separation (with centrally placed disc valves);

(b) by the valve member mounting support (cages, clamps); and (c) by the complete valve body, which consists of valve seating and suture ring.

Contrary to the properties of existing artificial heart valves, natural valves permit a central, undisturbed flow with a smooth opening and closing action and without any back flow. A further great disadvantage of most artificial heart valves is the psychological stress suffered by patients during the noise of opening and closing.

It can therefore be summarised that the currently used types of valves do not satisfactorily comply with functional requirements. The reasons for defects in known valves can be summarised as follows:

(a) Pressure gradients, which cause increased pumping work, loss of efficiency and insufficient inflation of the heart chamber;

(b) high localised shear stress which causes damage or destruction of the cellular blood components;

(c) back flow on closing of the valve of the order of 5% to 10%, and (d) formation of thromboses in areas of low speed of flow.

The invention is based on the problem of producing a closure device suitable for replacing the valves in human hearts, and especially suitable for the mitral and tricuspid valves, with which the disadvantages previously pointed out can be overcome and in particular a smooth, undisturbed flow both in the open and closed positions can be achieved and "dead water" zones causing thromboses and also high shear stress which is harmful to the blood can be avoided.

SUMMARY OF THE INVENTION

According to the invention there is provided a prosthetic closure device to replace the valves in human hearts, in particular the mitral and tricuspid valves, having a valve body in the form of a ring, a suture ring for attaching the valve body to the tissue and a valve member positioned in the valve body, wherein the valve member is in the form of a spherical segment having a diameter of substantially $1.058 \, D_{ri}$ and generally comprises part of the surface of a hollow sphere having a diameter of substantially $2D_{ri}$, where $D_{ri}$ is the smallest inner diameter of the valve body.

Contrary to the known disc valves, the valve member according to the invention is of dish-shaped formation, that is, in the form of a sperical segment. Being in the form of a spherical segment serves on the one hand to increase the strength of the valve member (in the closed position differences in pressure of up to 300 mm Hg can occur) and on the other hand has functional reasons which are explained below, taking the mitral valve as an example. When the ventrical fills, the mitral valve opens very quickly. The flow of blood entering the ventrical reaches the top of the chamber, spreads out sideways and upwards behind the two natural valve flaps and produces at the same time a strong ring vortex in the expanding ventrical, which holds the two flaps in a stable position. When the inflow slows down, the pressure difference on both sides of the flaps causes a movement towards the closed position. Thereby the mitral valve is already closed before the contraction of the ventrical and therewith the outflow phase begins.

These functional relationships lead to the conclusion that only a heart valve having a closure element of approximately the same form and dimensional position as the large flap of the mitral valve is in a position to make this above-mentioned physiological dynamic flow phenomenon effective. This apsect is taken into account in the construction according to the invention. It has been shown that the vortex produced behind the dish causes the valve to close before the start of the ventrical contraction. The diameter of the spherical segment is of the order of the size of the vortex diameter, whereby the dish adapts harmoniously to the above-mentioned physiological flow path.

With the solution according to the invention, anatomical, physiological and biochemical criteria are taken into consideration. The construction guarantees in particular a smooth, undisturbed flow both in the open and also in the closed positions, and thereby avoids "dead water" zones leading to thromboses and high shear stresses which are harmful to the blood. Moreover, the closure device according to the invention permits a central flow without any obstruction in the bloodstream, simulates the physiological flow inside the heart chambers, uses the accompanying flow power during the closing process, thereby reducing or eliminating the back flow, closes absolutely tight and works noiselessly.

The closure device according to the invention fulfils the following requirements:
(a) undisturbed flow in the open position, since the dish is wide open and substantially parallel to the inflow direction;
(b) minimal flow resistance and good conduction of the blood to the outflow tract in the closed position, since the dish is then fully embedded in the valve ring and lies parallel to the valve surface;
(c) low shear stress on account of the large opening surface and avoidance of obstructions to flow in the bloodstream;
(d) no "dead water" zones, since there are no flow obstructions;
(e) production and use of the chamber vortex to support the end of the valve; and
(f) completely tight closure.

The closure element according to the invention works in the following way:

When the pressure on the convex side of the valve exceeds the pressure on the concave side, the valve opens wide. The opening angle $\alpha$ is therefore determined by the amount of blood flowing in and the pressure difference available. Once the opening angle has reached about 45°, the area between the edge of the valve member and the valve body, which defines the free flow cross-section at smaller opening angles, corresponds to the cross-sectional area of the opening in the valve body. The blood then flows completely unobstructed by any elements through the opening cross-section and forms a vortex behind the dish in the concave area.

The thickness s of the valve member preferably amounts to less than 0.3–0.4 mm. This has the advantage that, compared to traditional valves, very short opening and closing times can be achieved, since the moment of inertia of the thin dish is very small in comparison with spherical or disc valves. This fact guarantees that the valve can react almost instantaneously to the quickly changing pressure gradients inside the heart chamber and thus resembles the natural valve more closely than any other existing artificial heart valve.

Furthermore the valve member is preferably connected to the valve ring by a hinge and is truncated in the area of the hinge. In contrast to the known spherical or disc valves, no flow obstructions in the flow path occur during the inflow phase, whereas these are unavoidable with traditional types of valves because of the presence of cages, clips etc. The appropriate length of the hinge area should be $k = 0.4 - 0.5\ D_{ri}$.

With regard to the special formation of the hinge, the valve is pivoted on the valve ring preferably by means of a small flat flap which enters the area k through a slot in the valve ring and is fastened with this on the outer side of the valve ring.

The advantages relating to the removal of any flow obstructions in the flow path are especially in evidence in a preferred construction in which the inner surface of the valve ring narrows conically in the direction of inflow and subsequently widens in such a way that a substantially annular seating for the valve member is formed. In this form the valve member is pivoted on the valve ring at the end area of the contact surface.

The form of the device described above is also especially advantageous with regard to a tight closing of the valve. When the pressure difference reverses above the valve, there results a quick closure, and the dish is supported on the seating and is at the same time centralised. The inflow region in the valve ring itself is of slightly conical shape (10°–15°) to obtain a better flow.

The valve ring is preferably provided on its outer side with a channel-like recess for holding the suture ring. The shape of the suture ring depends on the area of implantation in the heart and is not a subject of the invention. The suture ring consists, as is usually the case, of knitted or woven polyester material.

With regard to the material for the valve member, this advantageously comprises metal coated on both sides with blood-compatible synthetic material. Naturally other suitable materials, such as synthetic, ceramic or similar materials can be used instead of metal. The metallic valve is in particular coated with the blood-compatible material by a dipping process. In order to guarantee good contact of the synthetic material with the metal, before coating the valve member with the blood-compatible synthetic material it is first coated with a 1 $\mu$m thick layer of a special epoxy compound. Therefore with this special form of the device the valve member comprises a metal substrate with a first layer about 1 $\mu$m thick of an epoxy compound and a second layer of blood-compatible synthetic material. In order to further improve the adhesion of the synthetic material to the metal, the metal substrate is preferably provided with a number of apertures arranged in concentric circles, by means of which connection between the layers of synthetic material on both sides is produced. The hinge flap is advantageously formed in one piece with the valve member and consists of the same blood-compatible synthetic material with which the valve member is coated. It is preferably integrally cast in the course of the above-mentioned coating process, so that it is connected with the valve member without transition.

The valve ring advantageously consists of metal and is coated with the same blood-compatible synthetic material as the valve member. In this case also, synthetic, ceramic or similar materials can be used instead of metal.

Thereby three advantages are obtained at the same time:
(a) the direct contact of synthetic material to metal between the valve member and valve ring is avoided (low amount of friction),
(b) the sealing effect is improved with the smooth synthetic material, and
(c) development of noise is reduced.

BRIEF DESCRIPTION OF THE DRAWINGS

FIG. 1 is an underneath plan view of a prosthetic closure device in accordance with the invention, FIG. 2 is a cross-sectional view of the device taken along the line II—II of FIG. 1, and FIG. 3 is a detailed, partial cross sectional view taken along the line III—III of FIG. 1.

DETAILED DESCRIPTION OF THE PREFERRED EMBODIMENT

As shown in FIG. 1, the closure device comprises a valve body 2 in the form of a ring, a suture ring 3 fixed around the circumference of the valve body 2 and which serves to hold the closure device in the tissue, and a valve member 1 located in the valve body 2. The valve member 1 is in the form of a dish having a diameter $D_{disc} = 1.058 \, D_{ri}$ and generally comprises part of the surface of a hollow sphere having a diameter $D_{sph} = 2 \, D_{ri}$, where $D_{ri}$ is the smallest inner diameter of the valve ring 2. The valve member 1 is connected to the valve ring 2 by a hinge 4 and is truncated in the region of the hinge 4 to form a straight edge. The hinge 4 has a length $k = 0.4$–$0.5 \, D_{ri}$.

In FIG. 2 the closure device is shown in cross-section along the line II—II of FIG. 1. The open position of the valve member 1 is indicated by dotted lines. It can be seen that the valve ring 2 is formed in such a way that its inner surface 6 narrows conically in the direction of flow and subsequently widens so that an annular valve seating 9 ($D_{disc}$-$D_{ri}$) for the valve member 1 is formed. In the area of the hinge 4 the valve member 1 is provided with a small flap of synthetic material 7 serving as a hinge and extending beyond the edge of the valve member 1. By means of this flap of synthetic material 7 the valve member 1 is hinged to the valve ring 2 in the region of the valve seating 9, as shown at the left-hand side of FIG. 2. The valve ring 2 is provided with a slot 8 in the region of the hinge 4, which extends through the valve ring 2. The flap of synthetic material 7 is drawn through this slot 8 and is fastened on the outer side of the valve ring in a channel-like recess 10 which is provided to hold the suture ring 3. Thereby the flap of synthetic material 7 is held in position between the valve ring 2 and the suture ring 3. In this way an efficient attachment of the valve member 1 to the valve ring 2 is ensured, without any obstructions to the flow occurring in the flow path.

The valve member 1 illustrated in the drawings comprises a metallic material 12, which is coated on both sides with a blood-compatible synthetic material 14. In order to obtain better adhesion of the layer of blood-compatible synthetic material 14 to the metal substrate 12, the metal substrate is coated with a layer 16 approximately 1 μm thick of an epoxy compound and furthermore is provided with a number of apertures 5 arranged in concentric circles, which enable the layers of synthetic material on each side of the metal substrate to be interconnected. In the finished valve member these apertures are completely filled with synthetic material 14.

The closure device described above was submitted to the following test, together with a Björk-Shiley disc valve, one of the most widely known artificial valves:

(1) Measurements in pulsating, physiological flow in a closed-circuit simulator (pulse volume 80 cm³, pulse frequency 70/min, mitral position).

|  | Closure device according to the invention ($D_{ri}$ = 27 mm) | Bjork-Shiley disc valve ($D_{ri}$ = 27 mm) |
| --- | --- | --- |
| Peak opening pressure (mmHg) | 10.1 | 21.1 |
| Average pressure difference during opening phase (mmHg) | 0.75 | 2.45 |
| Average energy loss during opening phase (joules) | $0.8 \times 10^{-2}$ | $2.6 \times 10^{-2}$ |
| Back flow due to leakages | 0% | 10% |

The closure device according to the invention was moreover submitted to a fatigue test, with a stress cycle frequency of 700/min and a pressure difference of 130 mmHg, which commenced on the Nov. 22, 1977. This test produced about 1 million stress cycles per day.

The number of stress cycles completed up to the Mar. 3, 1978 was 98 million, which corresponds to a life span of 2.6 years with normal frequency of 70/min. Up until that date no appearance of fatigue had been observed at all. The life span aimed at is 10 years (367 million stress cycles) at normal frequency.

The results given above show that the closure device according to the invention possesses essentially better properties than the disc valve which has been most widely known.

We claim:

1. A prosthetic heart valve for controlling the flow of blood, said valve comprising:
    a ring-like valve body through which the blood flows; and
    a dome-like valve member in said body, said valve member being formed as a segment of a hollow sphere and presenting a convex surface to the blood in its normal direction of flow through the valve,
    said valve member being connected to the said valve body by a hinge for pivotal movement between an open position permitting blood flow through said body and a closed position in which said member rests on a generally annular supporting surface in the interior of said valve body to block blood flow, said hinge including a flexible flap affixed to a portion of the periphery of said valve member, said flap extending through a slot in said valve body and being secured to the exterior thereof.

2. A heart valve according to claim 1 wherein said valve member is truncated and said valve body is flattened in the region of said hinge.

3. The heart valve according to claim 2 wherein said hinge has a length within a range of 0.4 $D_{ri}$ to 0.5 $D_{ri}$, wherein $D_{ri}$ is the smallest inner diameter of said valve body.

4. The heart valve according to claim 1 wherein said valve member generally represents that part of the surface of a hollow sphere having a diameter $D_{sph} = 2 \, D_{ri}$ which is intersected by a circle of the diameter $D_{disc} = 1.058 \, D_{ri}$, wherein $D_{ri}$ is the smallest inner diameter of said valve body.

5. The heart valve according to claim 1 wherein the thickness of said valve member is less than 0.4 mm.

6. The heart valve according to claim 1 wherein said valve member comprises a metal sheet coated on both sides with a blood-compatible synthetic material.

7. The heart valve according to claim 6 wherein said flexible flap is integrally formed with said valve member and consists of the same blood-compatible synthetic material as that by which the metal substrate is coated.

8. The heart valve according to claim 6 wherein said valve member has a layer of epoxy compound intermediate said metal sheet and blood-compatible synthetic material.

9. The heart valve according to claim 6 wherein said metal sheet has a plurality of apertures through which the layers of synthetic material on both sides of said sheet are interconnected.

10. The heart valve according to claim 1 further including a suture ring on the exterior of said valve body for attaching the valve body to the tissue of the heart.

11. The heart valve according to claim 10 wherein said valve body has a channel-like recess on its exterior for receiving the suture ring.

12. The heart valve according to claim 1 wherein the interior of said valve body initially converges in the direction of blood flow and subsequently diverges to provide said annular supporting surface for said valve member.

13. The heart valve according to claim 12 wherein said slot for said flap is located in the diverging portion of the interior of said valve body.

14. The heart valve according to claim 6 wherein said valve body is formed of metal and is coated with the same blood-compatible synthetic material as said valve member.

* * * * *